US005478803A

United States Patent [19]

Boden et al.

[11] Patent Number: 5,478,803
[45] Date of Patent: Dec. 26, 1995

[54] 3,5-DIMETHYL-PENTENYL-DIHYDRO-2(3H)-FURANONE ISOMER MIXTURES, ORGANOLEPTIC USES THEREOF, PROCESS FOR PREPARING SAME AND PROCESS INTERMEDIATES THEREFOR

[75] Inventors: Richard M. Boden, Ocean; William J. Fylak, Loch Arbour; Marie R. Hanna, Keyport; Futoshi Fujioka, Oakhurst, all of N.J.

[73] Assignee: International Flavors & Fragrances Inc., New York, N.Y.

[21] Appl. No.: 330,847

[22] Filed: Oct. 27, 1994

[51] Int. Cl.[6] .......... A61K 7/46
[52] U.S. Cl. .......... 512/11; 549/295
[58] Field of Search .......... 247/295; 512/11

[56] References Cited

U.S. PATENT DOCUMENTS

| | | | |
|---|---|---|---|
| 4,420,622 | 12/1983 | van de Moesdijk et al. | 549/295 |
| 4,946,782 | 8/1990 | Farbood et al. | 435/126 |
| 4,960,597 | 10/1990 | Farbood et al. | 426/3 |
| 4,968,817 | 11/1990 | Brima | 549/295 |

FOREIGN PATENT DOCUMENTS

| | | | |
|---|---|---|---|
| 56-53673 | 5/1981 | Japan | 512/11 |

*Primary Examiner*—James H. Reamer
*Attorney, Agent, or Firm*—Arthur L. Liberman

[57] ABSTRACT

Described are 3,5-dimethyl-pentenyl-dihydro-2(3H)-furanone isomer mixtures defined according to the structure:

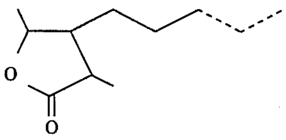

wherein structure represents mixtures wherein in the mixture in each of the compounds, one of the dashed lines represents a carbon-carbon double bond and the other of the dashed lines represents a carbon-carbon single bond, processes for preparing same and uses thereof in augmenting or enhancing the aroma of consumable materials including perfume compositions, colognes and perfumed articles (e.g., solid or liquid anionic, cationic, nonionic or zwitterionic detergents, hair preparations, fabric softeners, fabric softener articles, cosmetic powders and perfumed polymers). Also described is a process for preparing such 3,5-dimethyl-pentenyl-dihydro-2(3H)-furanone isomer mixtures using as a starting material 2,7-octadienol having the structure:

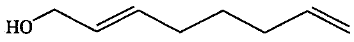

as well as the process intermediates having the structures:

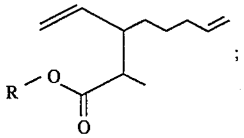

;

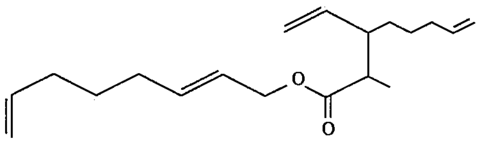

;

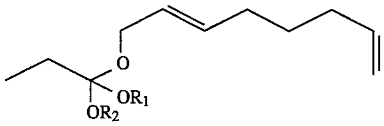

;

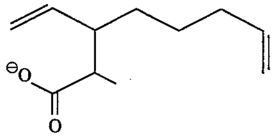

;

and

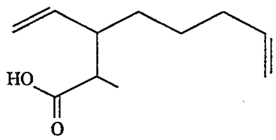

wherein R represents $C_1$–$C_4$ alkyl; $R_1$ and $R_2$ are the same or different and each represents 2,7-octadienyl or R.

6 Claims, 9 Drawing Sheets

GLC PROFILE FOR EXAMPLE I.

NMR SPECTRUM FOR EXAMPLE I, PEAK 12 OF FIG. I.

FIG. 4-A
GC PROFILE FOR EXAMPLE III.
(CAPILLARY COLUMN SURVEY).
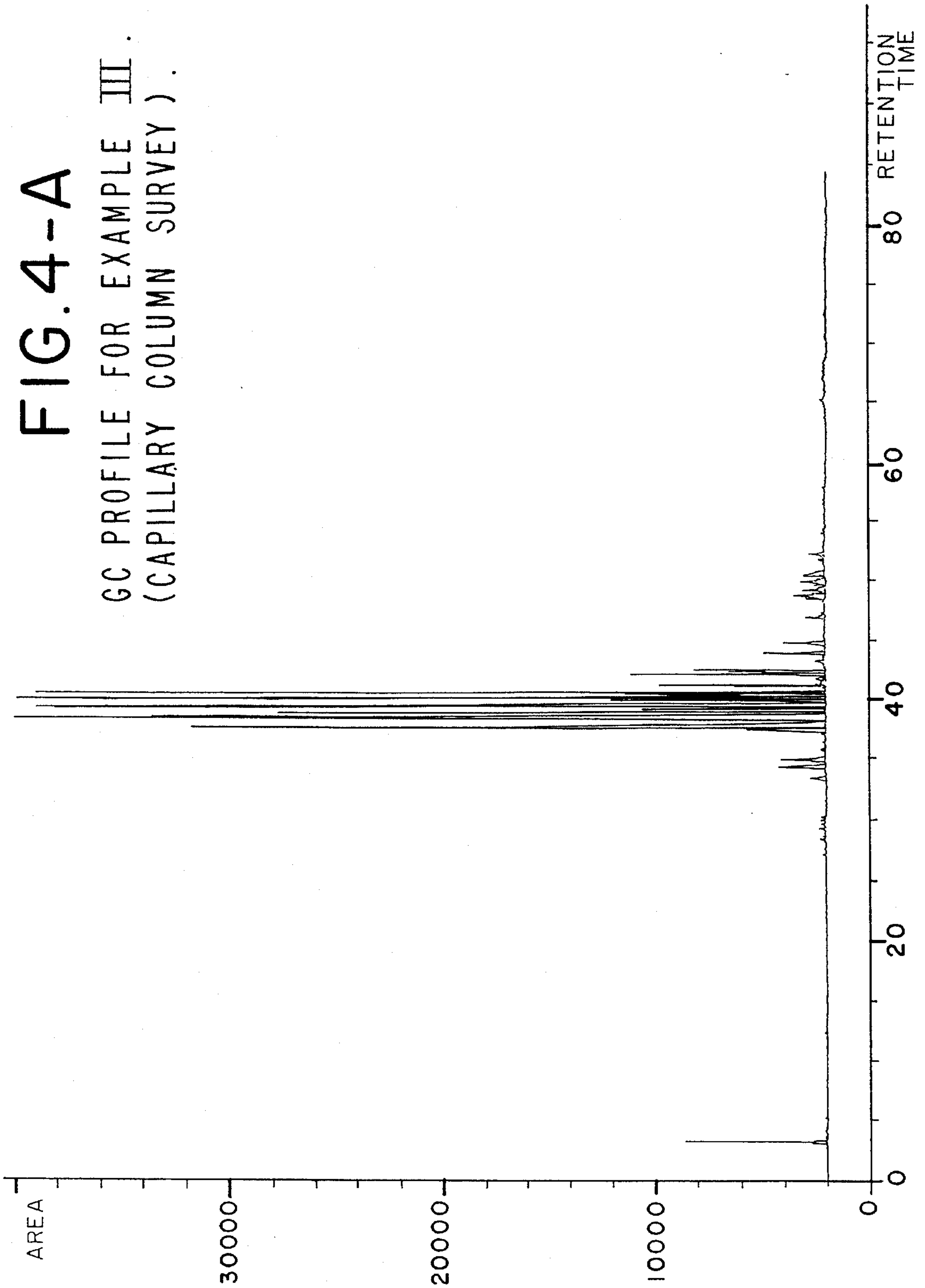

FIG.4-B
G C PROFILE FOR EXAMPLE III.
(CAPILLARY COLUMN SURVEY).
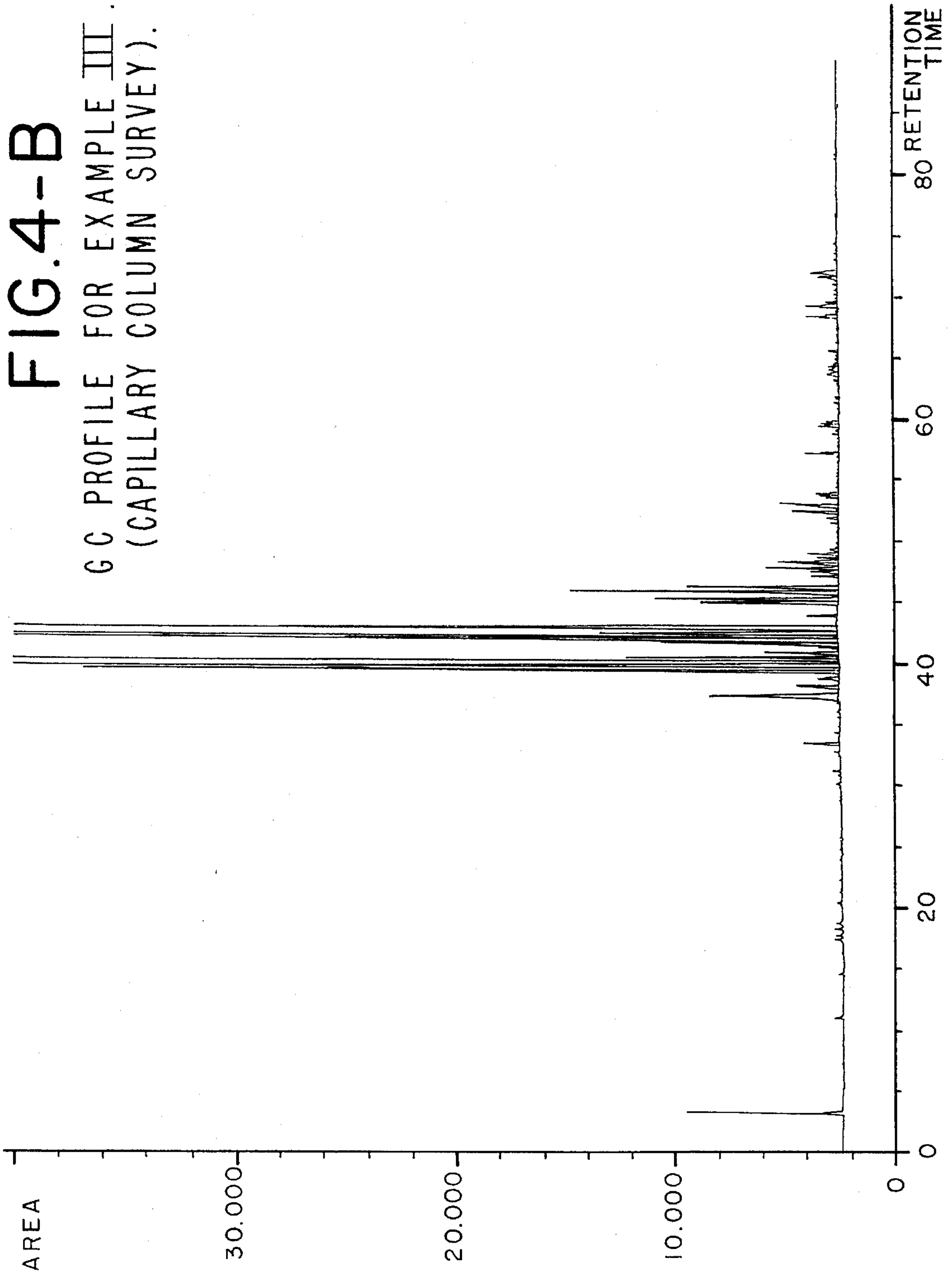

NMR SPECTRUM FOR EXAMPLE III.

FIG.5-A
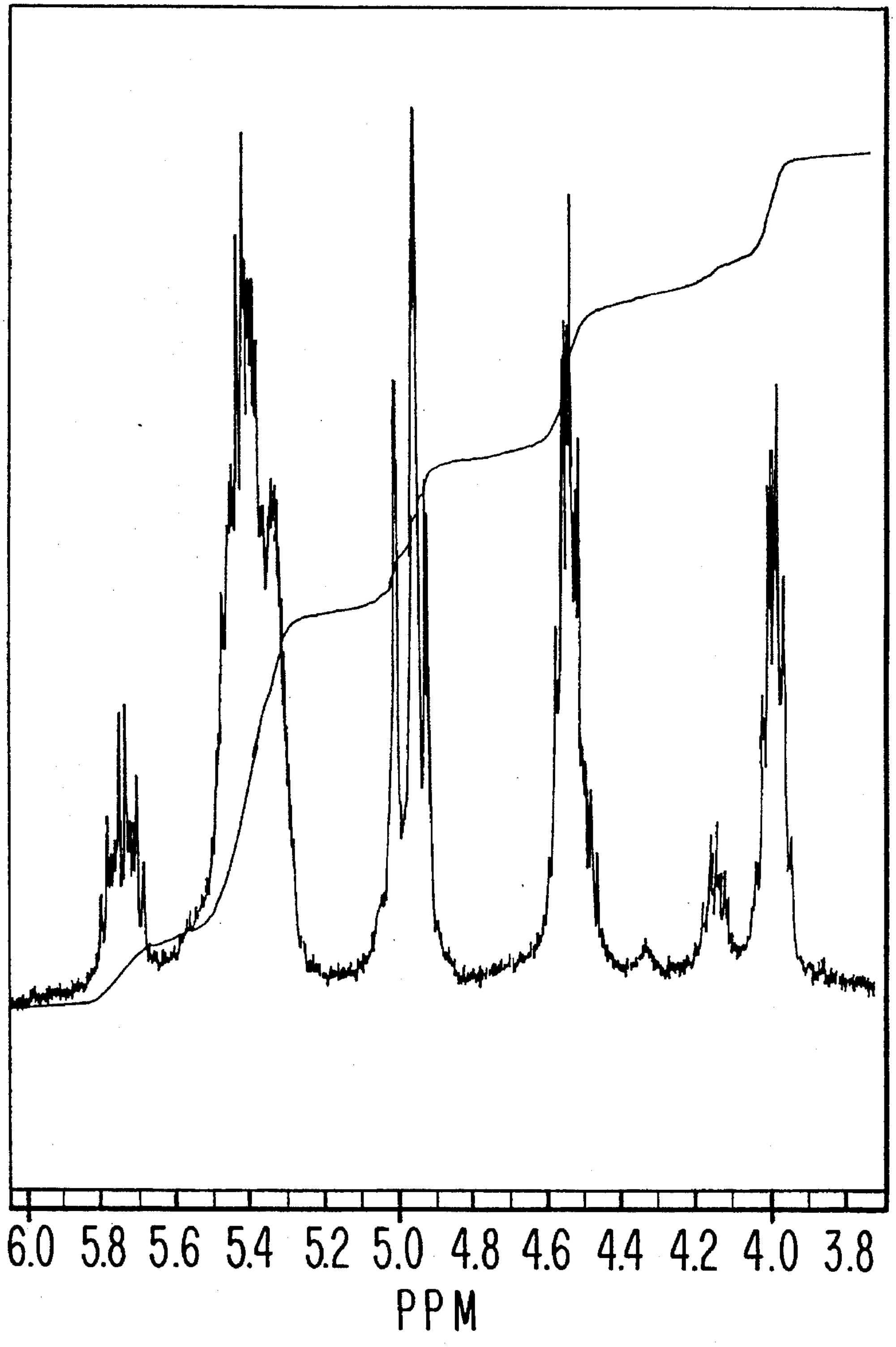

FIG. 5-B
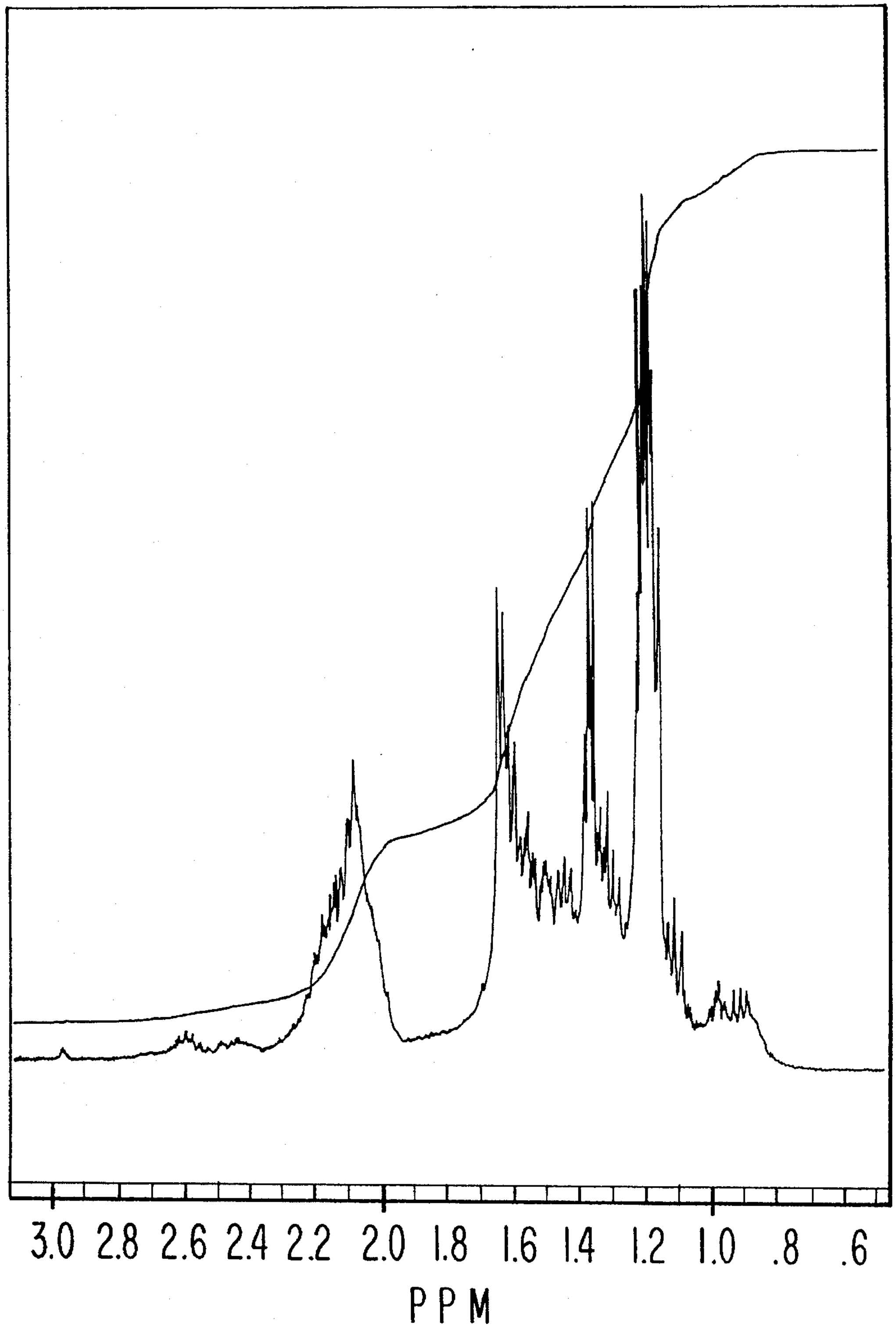

3,5-DIMETHYL-PENTENYL-DIHYDRO-2(3H)-FURANONE ISOMER MIXTURES, ORGANOLEPTIC USES THEREOF, PROCESS FOR PREPARING SAME AND PROCESS INTERMEDIATES THEREFOR

BACKGROUND OF THE INVENTION

The instant invention relates to 3,5-dimethyl-pentenyl-dihydro-2(3H)-furanone isomer mixtures defined according to the structure:

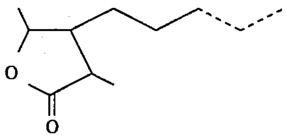

wherein the structure represents a mixture and wherein in the mixture in each of the compounds one of the dashed lines represents a carbon-carbon double bond and the other of the dashed lines represents a carbon-carbon single bond, processes for preparing same and organoleptic uses of said 3,5-dimethyl-pentenyl-dihydro-2(3H)-furanone isomer mixtures in augmenting or enhancing the aroma of consumable materials.

There has been considerable work performed relating to substances which can be used impart (modify, augment or enhance) fragrances to (or in) various consumable materials. These substances are used to diminish the use of natural materials some of which may be in short supply and to provide more uniform properties in the finished product.

Long-lasting, substantive and intense sweet, lactonic, coumarinic, jasmine aromas with intense green, citrusy, sweet, lactonic topnotes and bergamot peel and lemony undertones are highly desirable in several types of perfume compositions, perfumed articles, colognes, deodorizing compositions and odor maskant compositions.

The use of lactones for their organoleptic properties is well known and is documented in the literature. Lactones having unsaturated side chains are known for their uses particularly as flavorants. Thus, the compounds having the structures:

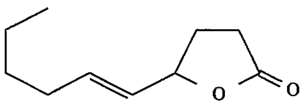

and

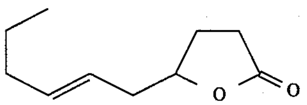

are disclosed in admixture with other lactones for their flavor uses in U.S. Pat. No. 5,110,953 issued on May 5, 1992.

Nothing, however, in the prior art sets forth the existence of the 3,5-dimethyl-pentenyl-dihydro-2(3H)-furanone isomer mixtures of our invention defined according to the structure:

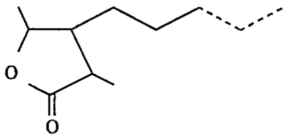

wherein the dashed lines are defined, supra. Nothing in the prior art sets forth the unexpected unobvious and advantageous organoleptic properties of the 3,5-dimethyl-pentenyl-dihydro-2(3H)-furanone isomer mixtures of our invention.

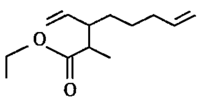

and

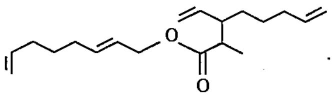

Figure 1:
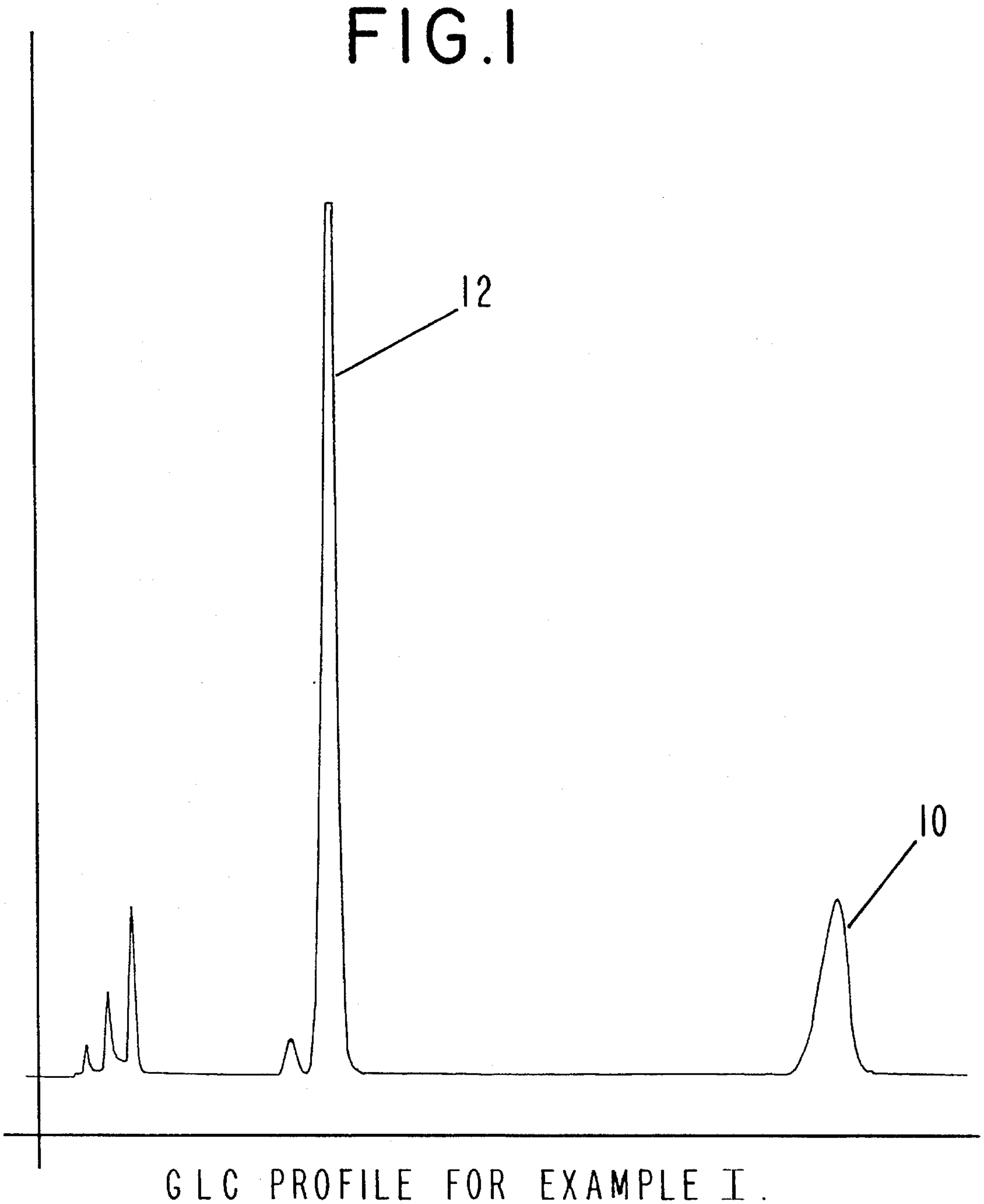
FIG. 1 is the GLC profile for the reaction product of Example I containing the compounds having the structures.
Figure 2:
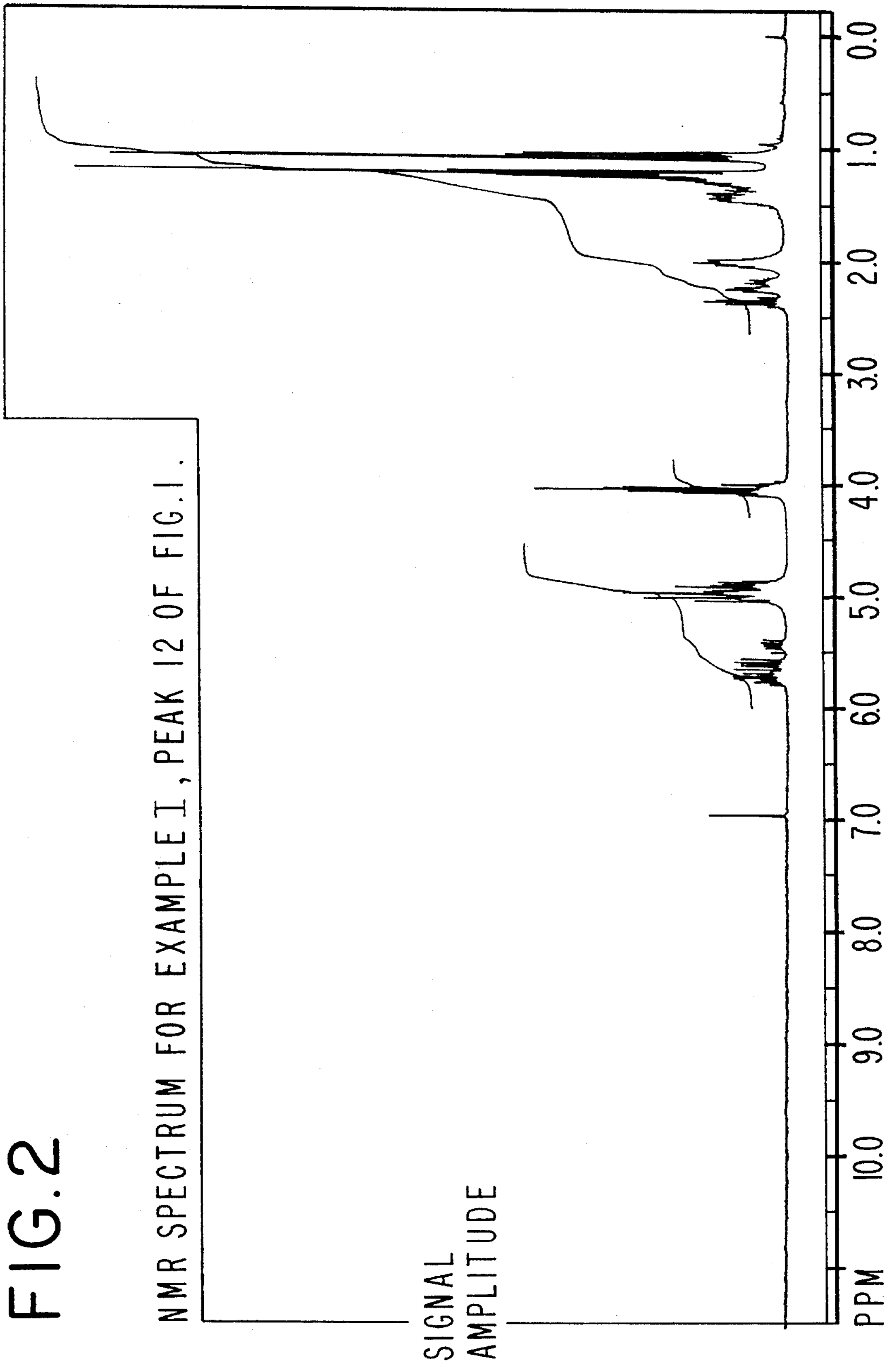

FIG. 2 is the NMR spectrum for the peak indicated by reference numeral 12 in the GLC profile of FIG. 1 for the compound having the structure:

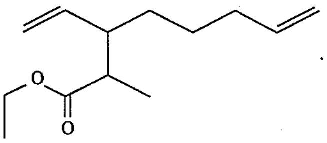

Figure 3:
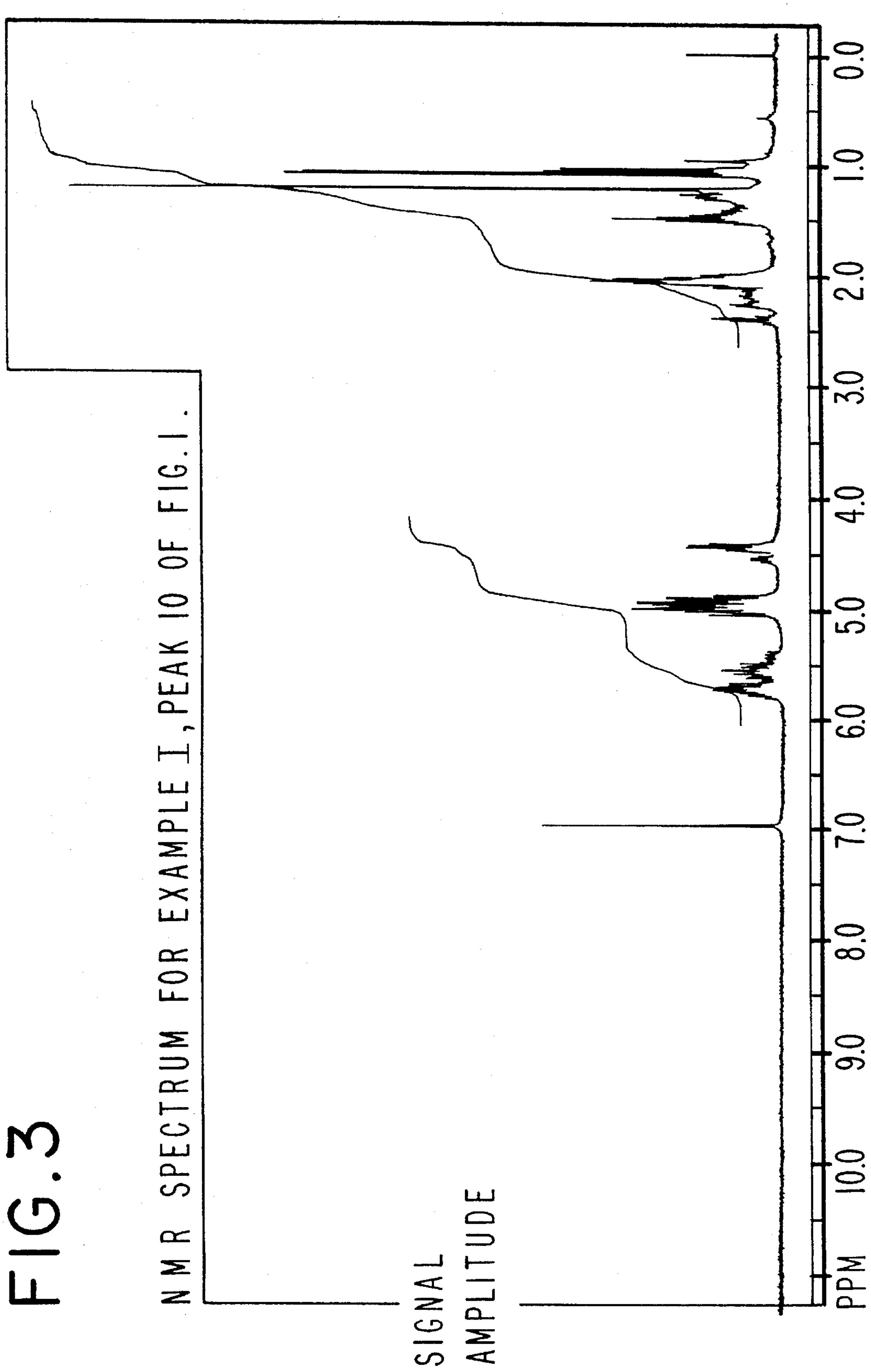

FIG. 3 is the NMR spectrum for the peak indicated by reference numeral 10 in the GLC profile of FIG. 1 for the compound having the structure:

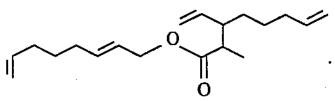

FIG. 4A is the GC profile (Capillary Column Survey) for the reaction product of Example III containing the isomers of the mixture defined according to the structure:

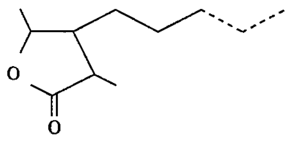

wherein in the mixture in each of the compounds one of the dashed lines is a carbon-carbon double bond and the other of the dashed lines is a carbon-carbon single bond. This mixture includes the compounds having the structures:

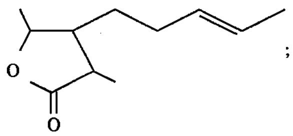
;

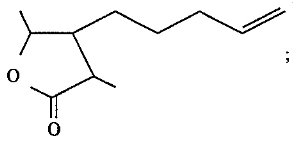
;

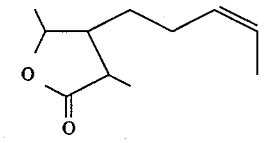

and

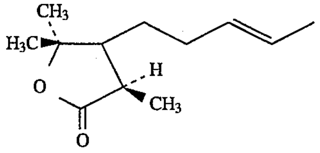

and other isomers. (Conditions: methyl silicone/bonded fused silica 50 meter×0.32 mm×0.5 um column programmed from 75°–225° C. at 2° C. per minute.)

FIG. 4B is a GC profile (Capillary Column Survey) for the reaction product of Example III using a carbowax 20M column containing nonbonded fused silica, 50 meters×0.32 mm× 0.3 um programmed from 75°–225° C. at 2° C. per minute.

Figure 5:
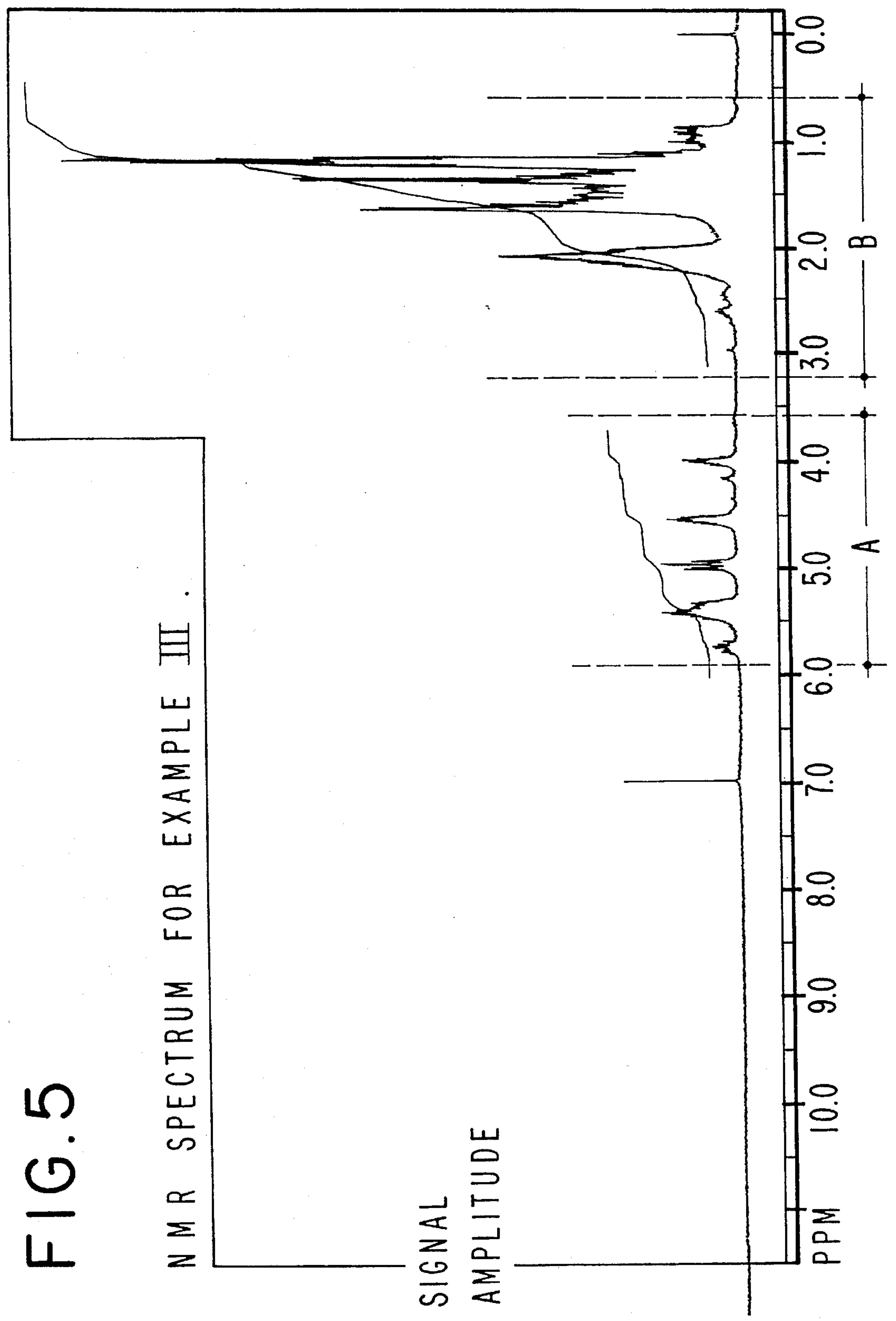

FIG. 5 is the NMR spectrum for the mixture of compounds defined according to the structure:

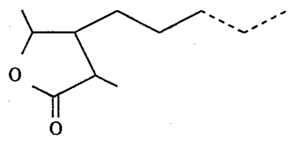

wherein in the mixture in each of the compounds one of the dashed lines is a carbon-carbon double bond and each of the other of the dashed lines is a carbon-carbon single bond.

FIG. 5A is an enlargement of the section indicated by the letter "A" in the NMR spectrum of FIG. 5.

FIG. 5B is an enlargement of the section indicated by the letter "B" in the NMR spectrum of FIG. 5.

Figure 6:
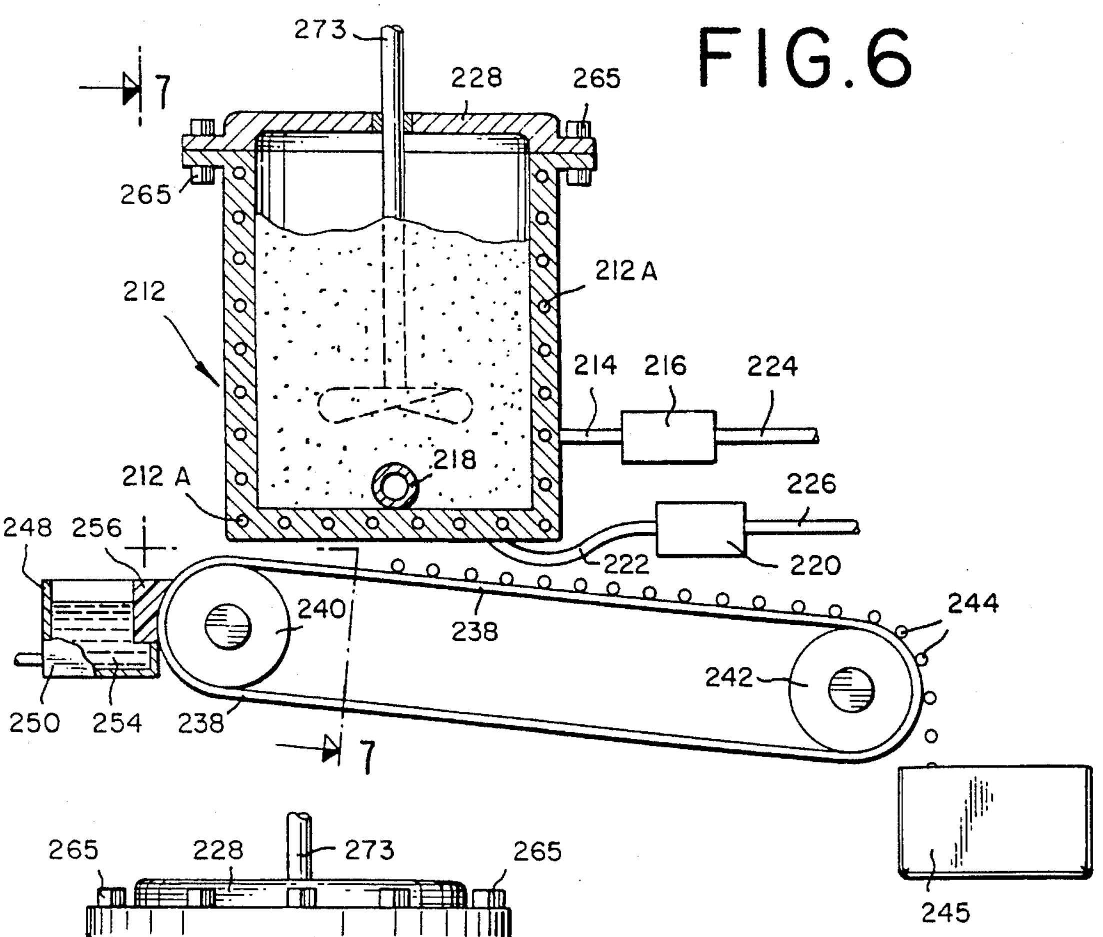

FIG. 6 is a partial side elevation and partial sectional view of an apparatus for forming polymer pellets containing the 3,5-dimethyl-pentenyl-dihydro-2(3H)-furanone isomer mixtures of our invention.

Figure 7:
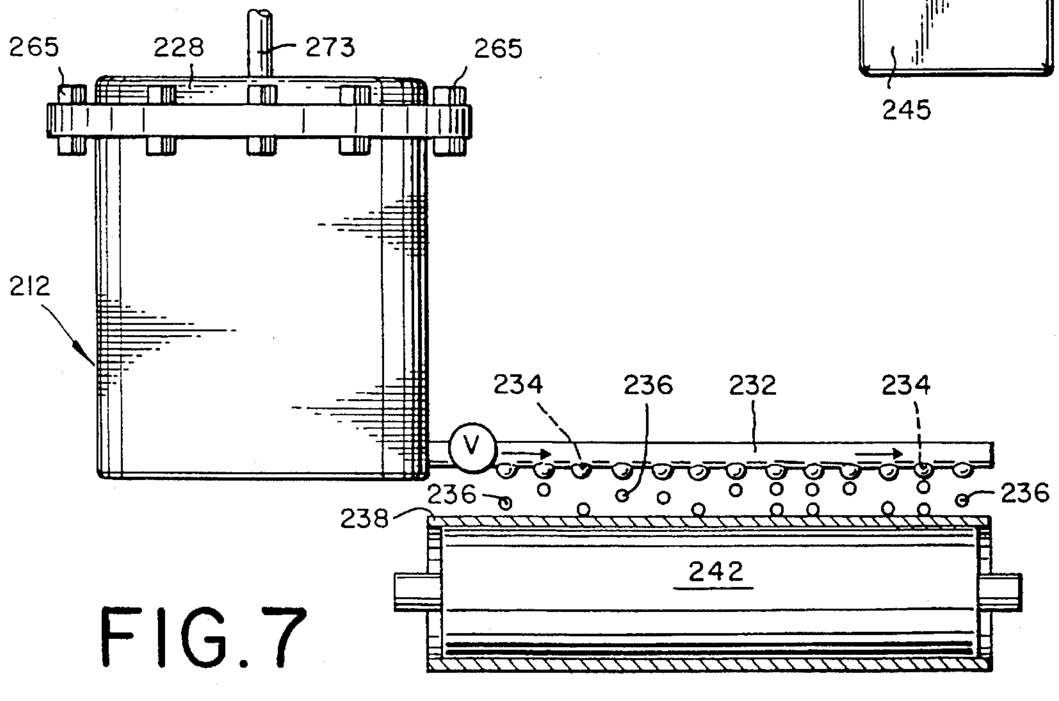

FIG. 7 is a section taken alone line 7—7 of FIG. 6.

DETAILED DESCRIPTION OF THE DRAWINGS

FIG. 1 is the GLC profile for the reaction product of Example I. The peak indicated by reference numeral 12 is the peak for the compound having the structure:

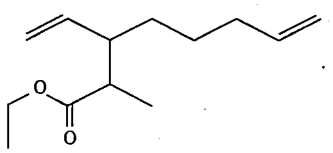
.

The peak indicated by reference numeral 10 is the peak for the compound having the structure:

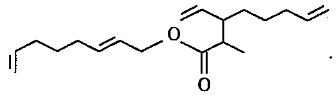
.

Referring to FIGS. 6 and 7, in particular, the apparatus used in producing polymeric fragrances containing the 3,5-dimethyl-pentenyl-dihydro-2(3H)-furanone isomer mixtures of our invention comprising a device for forming scented polyolefin (for example) pellets, which comprises a vat or container 212 into which a mixture of polyolefins such as polyethylene and an aromatic substance or scented material is placed (in this case the 3,5-dimethyl-pentenyl-dihydro-2(3H)-furanone isomer mixtures of our invention). The container is closed by an airtight lid 928 and clamped to the container by bolts 265. A stirrer 273 traverses the lid or cover 228 in an airtight manner and is rotated in a suitable manner. A surrounding cylinder 212 having heating coils 212A which are supplied with electric current through cable 224 from a rheostat or control 216 is operated to maintain a temperature inside the container 212 such that polyethylene or other thermoplastic polymer in the container will be maintained in the molten or liquid state. It has been found advantageous to employ a colorless odorless polymer (e.g., polyethylene) with viscosity ranging between 180 and 220 saybolt seconds and having a melting point in the range of 200°–280° F. The heating coils 212A are operated to maintain the upper portion of the container 212 within a temperature range of from 250°–350° F. The bottom portion of the container is heated by means of heating coils 212A heated through a control 220 connected thereto through a connecting wire 222 to maintain the lower portion of the container within a temperature range of from 250°–350° F.

Thus, polymer (e.g., polyethylene) is added to container 212 and is heated from 10–12 hours whereafter a scented aroma imparting material (the 3,5-dimethyl-pentenyl-dihydro-2(3H)-furanone isomer mixtures of our invention) is added quickly to the melt. The material must be compatible with the polyolefin and forms a homogeneous liquid melt therewith. The scented material is of a type for the particular aroma desired and formulated specifically for the scenting purpose for which the polyolefin will be employed.

Generally about 5–30% by weight of the scented material (containing the 3,5-dimethyl-pentenyl-dihydro-2(3H)-furanone isomer mixtures of our invention) is added to the polyolefin.

After the scent imparting material (e.g., a composition containing the 3,5-dimethyl-pentenyl-dihydro-2(3H)-furanone isomer mixtures of our invention) is added to the container 212, the mixture is stirred for a few minutes, for example, 5–15 minutes and maintained within the temperature range as indicated previously by heating coils 212A.

The controls and 220 are connected, respectively, through cables 214 and 222, respectively, to heating coils 212A. The said controls 216 and 220 are also connected through cables 224 and 226, respectively, to a suitable power supply of the electric current for supplying the electric power to the heating coils 212A for heating purposes.

Thereafter, the valve "V" is opened permitting the mass to flow outwardly through conduit 218/232 having a multiplicity of orifices 234 adjacent to the lower side thereof. The outer end of the conduit 218/232 is closed so that the liquid polymer (e.g., polyolefin) and aroma imparting material (e.g., the 3,5-dimethyl-pentenyl-dihydro-2(3H)-furanone isomer mixtures of our invention) will continuously drop through orifices 234 downwardly from conduit 232. During this time, the temperature of the polymer (e.g., polytheylene or polyolefin) and scent imparting material (e.g. the 3,5-dimethyl-pentenyl-dihydro-2(3H)-furanone isomer mixtures of our invention) is accurately controlled so that a temperature in the range of from about 210°–275° F. will exist in the conduit 218/232. The regulation of the temperature through the controls 216 and 220 is essential in order to insure temperature balance to provide for the continuous dropping or dripping of molten polymer (e.g., polyethylene) and scenting material (e.g., the 3,5-dimethyl-pentenyl-dihydro-2(3H)-furanone isomer mixtures of our invention) through the orifices 234 at a rate which will insure the formation of droplets 236 which will fall downwardly onto a moving conveyor belt 238 caused to run between conveyor wheels 240 and 242 beneath the conduit 232.

When the droplets 236 fall onto the conveyor belt 238, they form pellets 244 which harden almost instantaneously and fall off the end of the conveyor belt 238 into a container 245 and utilized in processes as illustrated, infra.

A feature of this aspect of the process of our invention is the provision for moistening of the convertor belt 238 to insure rapid formation of the solid polymeric (e.g., polyolefin) scented pellets 244 without sticking to material which will not normally stick to a melted plastic A moistening means 248 insures sufficiently cold temperature of the belt surface for adequate formation of the pellets 244. The adequate moistening means comprises a container 250 which is continuously fed with water 254 to maintain a level for moistening a sponge element 256 which bears against the exterior of the conveyor belt 238.

THE INVENTION

Our invention relates to the 3,5-dimethyl-pentenyl-dihydro-2(3H)-furanone isomer mixtures defined according to the structure:

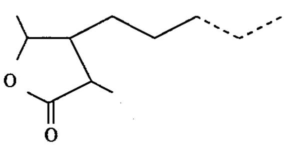

wherein in the mixture in each of the compounds one of the dashed lines represents a carbon-carbon double bond and the other of the dashed lines represents a carbon-carbon single bond and processes for preparing same and uses thereof in augmenting, enhancing or imparting aromas in or to perfumed compositions, perfumed articles and colognes.

Our invention also relates to the process intermediates defined according the structure:

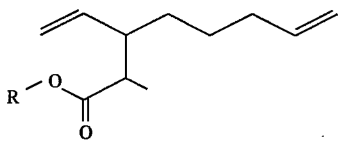

wherein R represents $C_1$–$C_4$ alkyl; the compound having the structure:

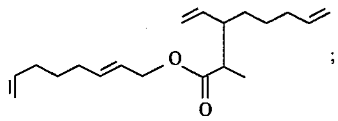

;

the compound having the structure:

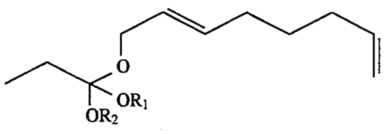

wherein $R_1$ and $R_2$ are the same or different and each represents R or 2,7-octadienyl; as well as the compound having the structure:

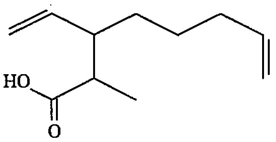

and the salt defined according to the anionic species having the structure:

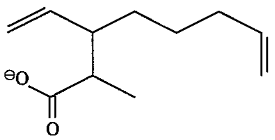

wherein the anionic species may be associated with an alkali metal such as sodium ion, potassium ion or lithium ion or an alkaline earth cation such as calcium or magnesium.

Thus, our invention is intended to cover the "compounds" defined thusly, in addition to the aforementioned structures:

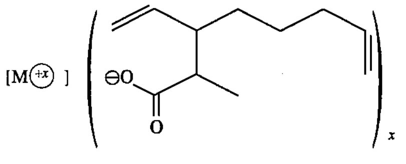

wherein x is an integer selected from the group consisting of 1 and 2 and M alkali metal or alkaline earth metal.

The compounds defined according to the structure:

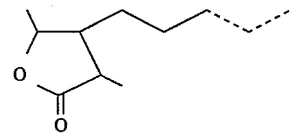

include but are not limited to the isomers having the structures:

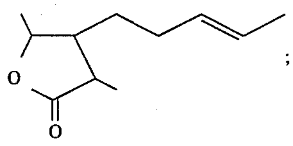

;

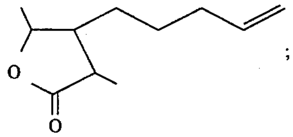

;

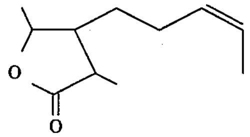

and

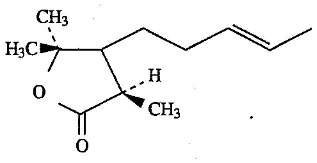

wherein the compound having the structure:

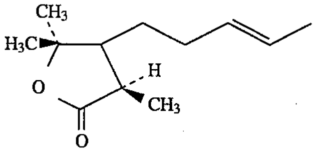

is representative of one of many stereoisomers included in the mixture of compounds defined according to the structure:

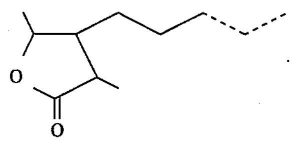

Our invention also relates to a process for preparing the 3,5-dimethyl-pentenyl-dihydro-2(3H)-furanone isomer mixtures of our invention defined according to the structure:

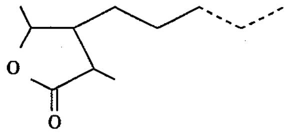

starting with 2,7-octadienol having the structure:

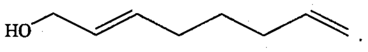

2,7-Octadienol is reacted with a compound having the structure:

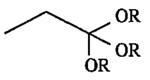

wherein R is $C_1$–$C_4$ alkyl, preferably ethyl according to the reaction:

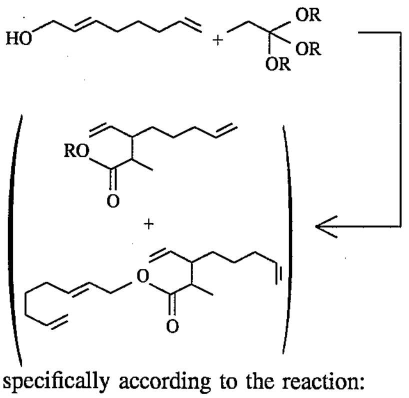

or more specifically according to the reaction:

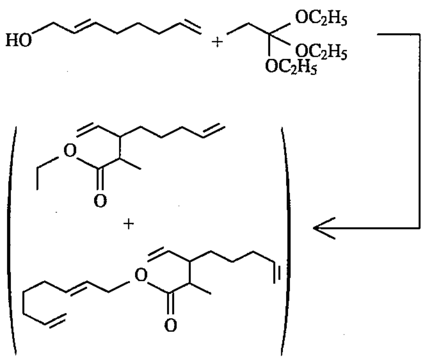

This reaction proceeds in two stages. The first stage takes place using an acid catalyst such as propionic acid, or other protonic acid catalyst or a Lewis acid catalyst such as boron trifluoride or boron trifluoride etherate catalyst. The first stage takes place at a temperature in the range of from 90°–145° C.

At the end of the first stage, a mixture Of compounds shown by the structure:

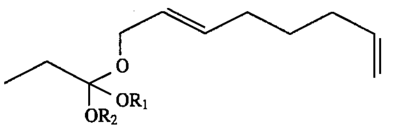

is formed wherein $R_1$ and $R_2$ in the mixture in each of the compounds are the same or different and each represents 2,7-octadienyl or R (with R being $C_1$–$C_4$ alkyl). The second stage takes place at a temperature in the range of from 145°–165° C. whereupon the compounds having the structures:

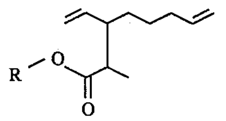

and

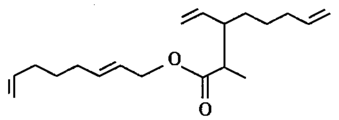

are formed. The resulting reaction mass is then washed and fractionally distilled yielding the compound having the structure:

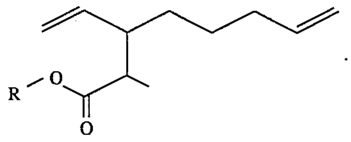

The compound having the structure:

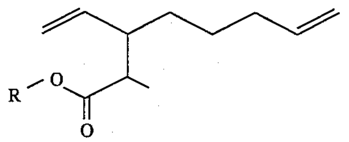

is then saponified using standard saponification reagents, preferably using a "phase transfer" reagent such as ALIQUAT® 336 (trademark of the Henkel Corporation of Minneapolis, Minn., tricapryl methyl ammonium chloride). The saponification reaction can take place using an alcoholic mixture of base such as a methanol mixture of potassium hydroxide with water according to the reaction:

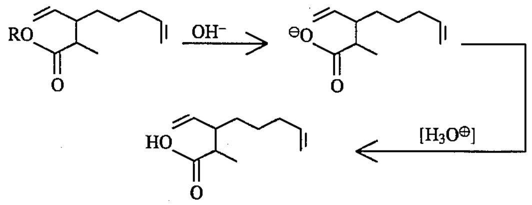

wherein R is $C_1$–$C_4$ alkyl. Specific examples of phase transfer agents useful in our invention are as follows:

"Tricapryl methyl ammonium chloride; Cetyl trimethyl ammonium chloride; Cetyl trimethyl ammonium bromide; and Benzyl trimethyl ammonium hydroxide.

In general, the phase transfer agents most preferred have the generic formula:

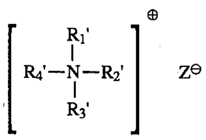

wherein at least one of $R_1'$, $R_2'$, $R_3'$ and $R_4'$ is $C_6$–$C_{14}$ aryl, $C_6$–$C_{10}$ aralkyl, $C_6$–$C_{20}$ alkyl, $C_6$–$C_{14}$ alkaryl and $C_6$–$C_{20}$ alkenyl and the other of $R_2'$, $R_3'$ and $R_4'$ is alkyl such as methyl, ethyl, n-propyl, i-propyl, 1-butyl, 2-butyl, 1-methyl-2-propyl, 1-pentyl and 1-octyl and Z- is an anion such as chloride, bromide and hydroxide."

After the salts defined according to the structure:

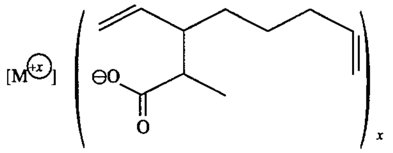

is formed, the salt is hydrolyzed to form the corresponding carboxylic acid intermediate having the structure:

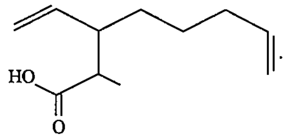

The saponification-hydrolysis reaction is shown thusly:

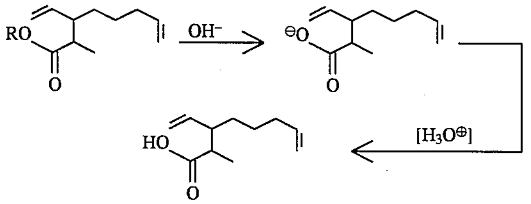

The acidification step (the second stage of the hydrolysis step) is carried out in aqueous acid such as 50% sulfuric acid or 50% hydrochloric acid.

The resulting product having the structure:

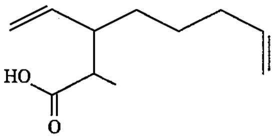

is then "lactonized" according to the reaction:

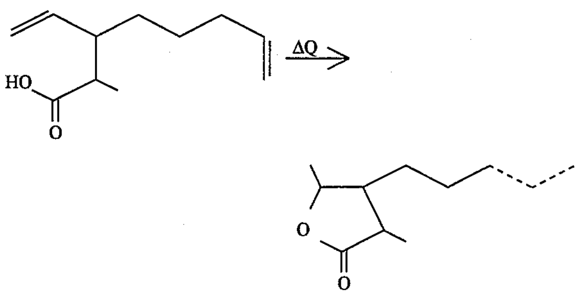

in the presence of strong acids such as 93% sulfuric acid; methane sulfonic acid, para,toluene sulfonic acid, xylene sulfonic acid and phosphoric acid. Again, the resulting product is "worked up" and fractionally distilled.

The resulting product, the 3,5-dimethyl-pentenyl-dihydro-2(3H)-furanone isomer mixture of our invention, defined according to the structure:

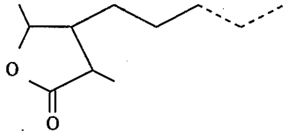

has a sweet, lactonic, coumarinic, jasmine aroma with intense green, citrusy, sweet, lactonic topnotes and bergamot peel and lemony undertones.

The 3,5-dimethyl-pentenyl-dihydro-2(3H)-furanone isomer mixtures of our invention can be used to contribute sweet, lactonic, coumarinic, jasmine aromas with intense green, citrusy, sweet, lactonic topnotes and bergamot peel and lemony undertones to perfume compositions, perfumed articles, colognes, deodorizing articles, deodorizing compositions and malodor maskants. Examples of perfumed articles are anionic, cationic, nonionic and zwitterionic detergents, drier-added fabric softener compositions and drier-added fabric softener articles as well as hair preparations. As olfactory agents, the 3,5-dimethyl-pentenyl-dihydro-2(3H)-furanone isomer mixtures of our invention can be formulated into or used as components of a "perfume composition" or can be used as components of a "perfumed article" or the perfume composition may be added to perfumed articles.

The term "perfume composition" is used herein to mean a mixture of organic compounds including, for example, alcohols, aldehydes (other than the aldehydes of our invention); ketones, nitriles (other than the nitriles of our invention), ethers, lactones, natural essential oils, synthetic essential oils, and frequently hydrocarbons which are admixed so that the combined odors of the individual components produce a pleasant and desired fragrance. Such perfume compositions usually contain (a) the main note or the "bouquet" or foundation stone of the composition; (b) modifiers which round off and accompany the main note; (c) fixatives which include odorous substances which lend a particular note to the perfume throughout all stages of evaporation and substances which retard evaporation; and (d) topnotes which are usually low-boiling, fresh smelling materials.

In perfume compositions, the individual component will contribute its particular olfactory characteristics, but the olfactory effect of the perfume composition will be the sum of the effects of each of the perfume ingredients. Thus, the 3,5-dimethyl-pentenyl-dihydro-2(3H)-furanone isomer mixtures of our invention can be used to alter the aroma characteristics of a perfume composition, for example, by highlighting or moderating the olfactory reaction contributed by another ingredient in the composition.

The amount of the 3,5-dimethyl-pentenyl-dihydro-2(3H)-furanone isomer mixtures of our invention which will be effective in perfume compositions, depends on many factors including the other ingredients, their amounts, and the effects which are desired. It has been found that perfume compositions containing as little as 0.5% of the 3,5-dimethyl-pentenyl-dihydro-2(3H)-furanone isomer mixtures of our invention or even less can be used to impart sweet, lactonic, coumarinic, jasmine aromas with intense green, citrusy, sweet, lactonic topnotes and bergamot peel and lemony undertones to soaps, liquid and solid, anionic, cationic, nonionic and zwitterionic detergents, cosmetic powders, liquid and solid fabric softeners, optical brightener compositions, perfumed polymers and other products. The amount employed can range up to 50% or higher and will depend on consideration of cost, nature of the end product and the effect desired on the finished product and the particular fragrance sought.

The 3,5-dimethyl-pentenyl-dihydro-2(3H)-furanone isomer mixtures of our invention can be used alone or taken together with other perfumery components in perfume compositions as an olfactory component in detergents and soaps, space odorants and deodorants; colognes, toilet waters, bath salts, hair preparations, such as lacquers, brilliantines, pomades and shampoos; cosmetic preparations such as creams, deodorants, hand lotions and sun screens; powders such as talcs, dusting powders, face powders and the like. When used as an olfactory component of a perfumed article, as little as 0.01% of one or more of the 3,5-dimethyl-pentenyl-dihydro-2(3H)-furanone isomer mixtures of our invention will suffice to impart sweet, lactonic, coumarinic, jasmine aromas with intense green, citrusy, sweet, lactonic topnotes and bergamot peel and lemony undertones. Generally, no more than 0.5% is required.

In addition, the perfume composition clan contain a vehicle or carrier for the 3,5-dimethyl-pentenyl-dihydro-2(3H)-furanone isomer mixtures taken alone or taken together with other ingredients. The vehicle can be a liquid such as an alcohol such as ethanol, a glycol, such as propylene glycol or the like. The carrier can be an absorbent solid such as a gum (e.g., gum arabic, guar gum and xanthan gum), or components for encapsulating the composition such as gelatin which can be used to form a capsule wall surrounding the perfume oil as by means of coacervation.

Our invention also relates to the utilization of controlled release technology for the controlled release of perfumes into gaseous environments; odor maskants and deodorizing agents into gaseous environments from polymers such as mixtures of epsilon polycaprolactone polymers and polyethylene which polyepsilon caprolactone polymers are described at Column 65 of U.S. Pat. No. 4,956,481 the specification for which is incorporated by reference herein.

Furthermore, the method of incorporating the 3,5-dimethyl-pentenyl-dihydro-2(3H)-furanone isomer mixtures of our invention or perfume compositions containing same into polymers may be according to the technique of U.S. Pat. No. 3,505 432 issued on Apr. 7, 1970 (the specification for which is incorporated by reference herein) or U.S. Pat. No. 4,274,498 issued Jan. 27, 1981, the disclosure of which is incorporated by reference herein.

Thus, for example, a first amount of liquid polyethylene-polyepsilon caprolactone polymer mixture (50:50) is mixed with the 3,5-dimethyl-pentenyl-dihydro-2(3H)-furanone isomer mixtures of our invention. Drops are formed from the mixture and the drops are solidified. The solidified drops are then melted, if desired, with a second amount of unscented low density polyethylene, for example, or polypropylene, for example. Usually, but not necessarily, the second amount of polymer is larger than the first amount. The resulting mixture thus obtained is solidified subsequent to or prior to ultimate casting into a utilitarian shape.

Thus, in accordance with one aspect of our invention the imparting of scent is effected in two stages. In a first stage, a 50:50 (weight:weight) polyepsilon caprolactone, e.g., PCL-700 (trademark of Union Carbide Corporation):polyethylene in molten form is admixed with a high percentage of the 3,5-dimethyl-pentenyl-dihydro-2(3H)-furanone isomer mixtures of our invention, e.g., the mixture of isomers defined according to the structure:

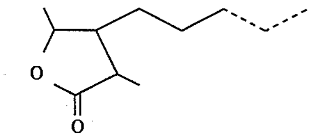

and the mixture is solidified in the form of pellets or beads. These pellets or beads thus contain a high percentage of 3,5-dimethyl-pentenyl-dihydro-2(3H)-furanone isomer mixtures (e.g., up to 45% by weight of the entire mixture) and may be used as "master pellets" which, thereafter, in a second stage, if desired, may be admixed and liquified with additional polymers such as additional polyethylene or mixtures of polyethylene and polyepsilon caprolactone in an unscented state, or unscented polypropylene.. In addition, additional polymers or copolymers may be used, for example, copolymers specified and described in United Kingdom Patent Specification No. 1,589,201 published on May 7, 1981.

In accordance with the present invention the 3,5-dimethyl-pentenyl-dihydro-2(3H)-furanone isomer mixtures of our invention are added to the polymer in a large closed container or drum which is maintained under controlled temperature conditions while the polymer in a melted condition is mixed with the 3,5-dimethyl-pentenyl-dihydro-2(3H)-furanone isomer mixtures of our invention under agitation.

In order that the perfume be added uniformly to the polymer, the temperature of the melt is constantly controlled during the process. The polymer-perfume mixture is then directed through an elongated conduit or pipe element having a plurality of orifices adjacent to the lower-most portion thereof. The polymer, enriched by the 3,5-dimethyl-pentenyl-dihydro-2(3H)-furanone isomer mixtures of our invention, is permitted to drip through the orifices onto a continuously moving, cooled conveyor upon which the polymer containing the 3,5-dimethyl-pentenyl-dihydro-2(3H)-furanone isomer mixtures of our invention solidifies into small size pellets with the perfume imprisoned therein. The apparatus useful in conjunction with this process advantageously includes a conveyor of material which will adhere to the polymer which contains the 3,5-dimethyl-pentenyl-dihydro-2(3H)-furanone isomer mixtures of our invention.

In order that the droplets form into uniform pellets or beads, the conveyor is continuously washed with a liquid such as water to maintain the surface relatively cool. The pellets are delivered by the conveyor into a container and packaged for shipment or for further incorporation into articles of manufacture, e.g., garbage bags (using the deodorization quality of the 3,5-dimethyl-pentenyl-dihydro-2(3H)-furanone isomer mixtures of our invention).

The following Examples I, II and III set forth the preparation the 3,5-dimethyl-pentenyl-dihydro-2(3H)-furanone isomer mixtures of our invention. Examples IV, et seq., set forth the organoleptic uses of the 3,5-dimethyl-pentenyl-dihydro-2(3H)-furanone isomer mixtures of our invention prepared according to Examples I, II and III.

The following Examples I, et seq., serve to illustrate our invention and this invention is to be considered to be restricted thereto only as indicated in the appended claims.

All parts and percentages given herein are by weight unless otherwise specified.

EXAMPLE I

PREPARATION OF ETHYL ESTER OF METHYL-3-VINYL-7-OCTENOIC ACID

Reaction:

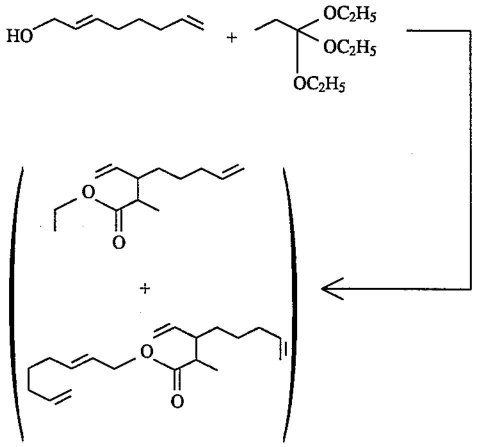

Into a 3 liter reaction vessel equipped with stirrer, thermometer, reflux condenser, heating mantle and addition funnel is charged 636 grams (5.05 moles) of 2,7-octadienol. The 2,7-octadienol is heated to 145° C. Over a period of 4 hours, a mixture of 10 grams of propionic acid and 891 grams (5.05 moles) of triethyl orthopropionate having the structure:

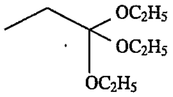

is added to the reaction mass with stirring.

At the end of the addition period, the reaction mass is heated at 143° C. for a period of 5.25 hours. At this point in time, a mixture of compounds defined according to the structure:

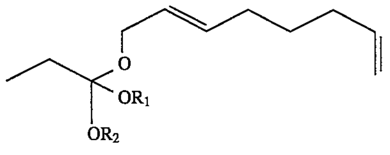

is formed wherein $R_1$ and $R_2$ are the same or different in each of the compounds in the mixture and each represents 2,7-octadienyl or ethyl.

The reaction mass is then heated to 165° C. and maintained at 165° C. for a period of 2 hours.

The reaction mass is then transferred to a separatory funnel and the reaction mass is admixed with an equal volume of saturated sodium chloride solution. The reaction mass is then washed with an equal volume of saturated sodium bicarbonate solution and then followed by washing with an equal volume of saturated sodium chloride solution.

The organic phase is then fractionally distilled yielding the following fractions:

| Fraction Number | Vapor Temperature (°C.) | Liquid Temperature (°C.) | Vacuum mm/Hg. Pressure |
|---|---|---|---|
| 1 | 30 | 88 | 78 |
| 2 | 42/77 | 75/85 | 3 |
| 3 | 84 | 112 | 2 |
| 4 | 92 | 110 | 3 |
| 5 | 103 | 120 | 3 |
| 6 | 98 | 125 | 5 |
| 7 | 64 | 140 | 4 |
| 8 | 150 | 171 | 4 |
| 9 | 150 | 205 | 4 |

Fractions 2–5 are bulked for use in Example II.

Fractions 2–5 is a mixture of isomers of the compound having the structure:

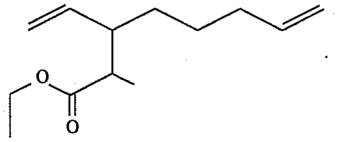

EXAMPLE II

PREPARATION OF 2-METHYL-3-VINYL-7-OCTANOIC ACID

Reaction:

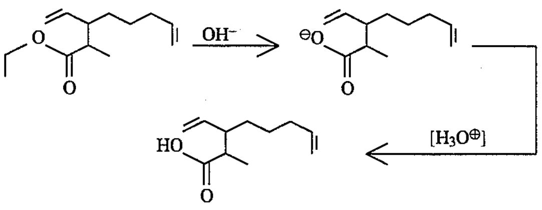

Into a 2 liter reaction flask equipped with stirrer, thermometer, reflux condenser and heating mantle are placed the following materials:

378 grams of the compound having the structure:

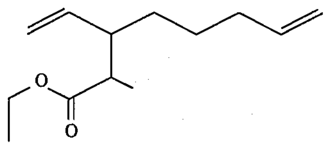

prepared according to Example I (bulked distillation fractions 2–5);

122 grams methanol;

122 grams water;

20 grams potassium hydroxide; and 15 grams ALIQUAT® 336 (tricapryl methyl ammonium chloride, trademark of the Henkel Corporation of Minneapolis, Minn.).

The reaction mass is heated to reflux with stirring and maintained at reflux for a period of 0.5 hours. 171 grams of potassium hydroxide and 15 additional grams of ALIQUAT® 336 is added to the reaction mass.

The reaction mass is refluxed for a period of 2 hours.

A 3 liter reaction flask equipped with stirrer, thermometer, reflux condenser and heating mantle is then charged with 200 grams of sulfuric acid and 200 grams of ice.

The reaction mass is then slowly added to the contents of the 3 liter reaction flask.

The resulting product is then fractionally distilled yielding the following fractions:

| Fraction Number | Vapor Temperature (°C.) | Liquid Temperature (°C.) | Vacuum mm/Hg. Pressure |
|---|---|---|---|
| 1 | 56 | 95 | 2 |
| 2 | 105 | 140 | 2 |
| 3 | 122 | 205 | 3 |

Fractions 1 and 2 are bulked for further reaction in Example III.

Fractions 1 and 2 are the compound having the structure:

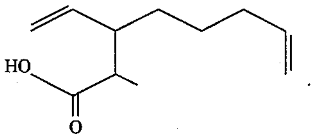

EXAMPLE III

PREPARATION OF 3,5-DIMETHYL-PENTENYL-DIHYDRO-2(3H)-FURANONE ISOMER MIXTURE

Reaction:

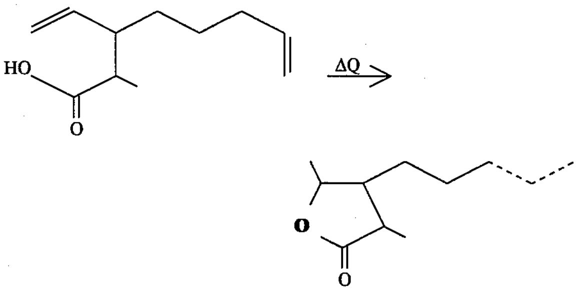

Into a 500 ml reaction vessel equipped with stirrer, thermometer, reflux condenser and heating mantle are placed:

138.5 grams of the compound having the structure:

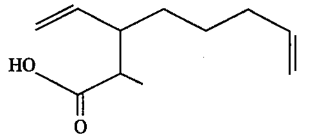

prepared according to Example II bulked distillation fractions 1 and 2;

1.3 grams of para-toluene sulfonic acid; and 100 ml toluene.

The reaction mass is heated with stirring for a period of 2 hours.

The reaction mass is then admixed with an equal volume of water and the organic phase is separated from the aqueous phase. The organic phase is washed with an equal volume of saturated sodium bicarbonate and the aqueous phase is separated from the organic phase. The organic phase is then washed with an equal volume of saturated sodium chloride and the organic phase is separated from the aqueous phase. The organic phase is then fractionally distilled on a 2-inch splash column yielding the following fractions:

| Fraction Number | Vapor Temperature (°C.) | Liquid Temperature (°C.) | Vacuum mm/Hg. Pressure |
|---|---|---|---|
| 1 | 30 | 48 | 95 |
| 2 | 23 | 56 | 3 |
| 3 | 101/108 | 118/127 | 2 |
| 4 | 111 | 178 | 2 |
| 5 | 115 | 198 | 2 |

Fractions 3 and 4 are bulked. Bulked distillation fractions are the mixture of isomers defined according to the structure:

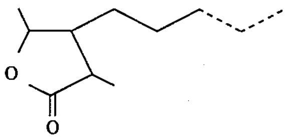

wherein in each of the compounds one of the dashed lines is a carbon-carbon double bond and the other of the dashed lines is a carbon-carbon single bond.

Bulked distillation fractions 3 and 4 have a sweet, lactonic, coumarinic and jasmine aroma with intense green, citrusy, sweet, lactonic topnotes and bergamot peel and lemony undertones.

EXAMPLE IV

ROSE PERFUME

A rose perfume is prepared containing the following ingredients:

| Ingredients: | Parts by Weight |
|---|---|
| Rhodinol | 250 |
| Phenylethyl alcohol (beta) | 195 |
| Alpha methyl ionone | 80 |

-continued

| Ingredients: | Parts by Weight |
|---|---|
| Linalyl acetate | 60 |
| Cis-3-hexenyl acetate | 5 |
| Jasmine absolute | 10 |
| Cinnamic alcohol | 20 |
| Rhodinyl acetate | 60 |
| Cyclohexyl ethyl alcohol | 20 |
| Geraniol | 130 |
| Geranyl acetate | 80 |
| Paraisopropyl cyclohexanol | 60 |
| Diethyl phthalate | 30 |
| Trans,trans-delta-damascone | 30 |
| The 3,5-dimethyl-pentenyl-dihydro-2(3H)-furanone isomer mixture of Example III having the structure: 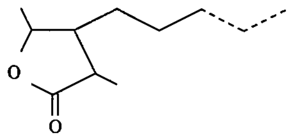 (bulked distillation fractions 3 and 4). | 30 |

The 3,5-dimethyl-pentenyl-dihydro-2(3H)-furanone isomer mixture of our invention produced according to Example III (bulked distillation fractions 3 and 4) imparts to this rose formulation sweet, lactonic, coumarinic, jasmine, bergamot peel and lemony undertones and intense green, citrusy, sweet, lactonic topnotes.

Accordingly, the organoleptic profile of the foregoing perfume composition can be described as:

"A rose aroma with sweet, lactonic, coumarinic, jasmine, bergamot peel and lemony undertones and intense green, citrusy, sweet and lactonic topnotes".

EXAMPLE V

PREPARATION OF COSMETIC POWDER COMPOSITIONS

Cosmetic powder compositions are prepared by mixing in a ball mill 100 grams of talcum powder with 0.25 grams of each of the substances set forth in Table I below. Each of the cosmetic powder compositions has an excellent aroma as described in Table I below:

TABLE I

| Substance | Aroma Description |
|---|---|
| The 3,5-dimethyl-pentenyl-dihydro-2(3H)-furanone isomer mixture defined according to the structure: 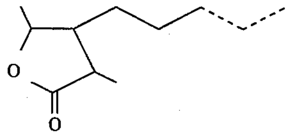 wherein in the mixture in each of the compounds one of the dashed lines is a carbon-carbon double bond and the other of the dashed lines is a carbon-carbon single bond | A sweet, lactonic, coumarinic and jasmine aroma with intense green, citrusy, sweet and lactonic topnotes and bergamot peel and lemony undertones. |

TABLE I-continued

| Substance | Aroma Description |
|---|---|
| prepared according to Example III bulked distillation fractions 3 and 4. | |
| Perfume composition of Example IV. | A rose aroma with sweet, lactonic, coumarinic, jasmine, bergamot peel and lemony undertones and intense green, citrusy, sweet and lactonic topnotes. |

EXAMPLE VI

PERFUMED LIQUID DETERGENTS

Concentrated liquid detergents (lysine salt of n-dodecylbenzene sulfonic acid as more specifically described in U.S. Pat. No. 3,948,818 issued on Apr. 6, 1976 incorporated by reference herein) with aroma nuances as set forth in Table I of Example V, are prepared containing 0.10%, 0.15%, 0.20%, 0.25%, 0.30% and 0.35% of the substance set forth in Table I of Example V. They are prepared by adding and homogeneously mixing the appropriate quantity of substance set forth in Table I of Example V in the liquid detergent The detergents all possess excellent aromas as set forth in Table I of Example V, the intensity increasing with greater concentrations of substance as set forth in Table I of Example V.

EXAMPLE VII

PREPARATION OF COLOGNES AND HANDKERCHIEF PERFUMES

Compositions as set forth in Table I of Example V are incorporated into colognes at concentrations of 2.0%, 2.5%, 3.0%, 3.5%, 4.0%, 4.5% and 5.0% in 80%, 85%, 90% and 95% aqueous food grade ethanol solutions; and into handkerchief perfumes at concentrations of 15%, 20%, 25% and 30% (in 80%, 85%, 90% and 95% aqueous food grade ethanol solutions). Distinctive and definite fragrances as set forth in Table I of Example V are imparted to the colognes and to the handkerchief perfumes at all levels indicated.

EXAMPLE VIII

PREPARATION OF SOAP COMPOSITIONS 100 grams of soap chips (per sample) (IVORY® produced by the Procter & Gamble Company of Cincinnati, Ohio) are each mixed with one gram samples of substances as set forth in Table I of Example V until homogeneous compositions are obtained. In each of the cases, the homogeneous compositions are heated under 8 atmospheres pressure at 180° C. for a period of 3 hours and the resulting liquids are placed into soap molds. The resulting soap cakes, on cooling, manifest aromas as set forth in Table I of Example V.

EXAMPLE IX

PREPARATION OF SOLID DETERGENT COMPOSITIONS

Detergents are prepared using the following ingredients according to Example I of Canadian Patent No. 1,007,948 (incorporated by reference herein):

| Ingredients | Percent by Weight |
|---|---|
| NEODOL ® 45-11 (a $C_{14}$–$C_{15}$ alcohol ethoxylated with 11 moles of ethylene oxide) | 12 |
| Sodium carbonate | 55 |
| Sodium citrate | 20 |
| Sodium sulfate, water brighteners | q.s. |

This detergent is a phosphate-free detergent. Samples of 100 grams each of this detergent are admixed with 0.10, 0.15, 0.20 and 0.25 grams of each of the substances as set forth in Table I of Example V. Each of the detergent samples has an excellent aroma as indicated in Table I of Example V.

EXAMPLE X

Utilizing the procedure of Example I at column 15 of U.S. Pat. No. 3,632,396 (the disclosure of which is incorporated herein by reference), non-woven cloth substrates useful as drier-added fabric softening articles of manufacture are prepared wherein the substrate, the substrate coating, the outer coating and the perfuming material are as follows:

1. A water "dissovable" paper ("Dissolvo Paper");
2. ADOGEN® 448 (m.p. about 140° F.) as the substrate coating; and
3. An outer coating having the following formulation (m.p. about 150° F.):
   57% $C_{20-22}$ HAPS
   22% isopropyl alcohol
   20% antistatic agent
   1% of one of the substances as set forth in Table I of Example V.

Fabric softening compositions prepared according to Example I at column 15 of U.S. Pat. No. 3,632,396 having aroma characteristics as set forth in Table I of Example V, supra, consist of a substrate coating having a weight of about 3 grams per 100 square inches of substrate; a first coating located directly on the substrate coating consisting of about 1.85 grams per 100 square inches of substrate; and an outer coating coated on the first coating consisting of about 1.4 grams per 100 square inches of substrate. One of the substances of Table I of Example V is admixed in each case with the outer coating mixture, thereby providing a total aromatized outer coating weight ratio to substrate of about 0.5:1 by weight of the substrate. The aroma characteristics are imparted in a pleasant manner to the head space in a drier on operation thereof in each case using said drier-added fabric softener, non-woven fabrics and these aroma characteristics are described in Table I of Example V, supra.

EXAMPLE XI

HAIR SPRAY FORMULATIONS

The following hair spray formulation is prepared by first dissolving PVP/VA E-735 copolymer manufactured by the GAF Corporation of 140 West 51st Street, New York, N.Y. in 91.62 grams of 95% food grade alcohol. The following ingredients are added to the PVP/VA alcoholic: solution:

| | |
|---|---|
| Dioctyl sebacate | 0.05 weight percent |
| Benzyl alcohol | 0.10 weight percent |
| Dow Corning 473 fluid (prepared by the Dow Corning Corporation) | 0.10 weight percent |
| TWEEN ® 20 surfactant (prepared by ICI America Corporation) | 0.03 weight percent |
| One of the perfumery substances as set forth in Table I of Example V | 0.10 weight percent |

The perfuming substances as set forth in Table I of Example V add aroma characteristics as set forth in Table I of Example V which are rather intense and aesthetically pleasing to the users of the soft-feel, good-hold pump hair sprays.

EXAMPLE XII

CONDITIONING SHAMPOOS

Monamid CMA (prepared by the Mona Industries Company) (3.0 weight percent) is melted with 2.0 weight percent coconut fatty acid (prepared by the Procter & Gamble Company of Cincinnati, Ohio); 2.0 weight percent ethylene glycol distearate (prepared by the Armak Corporation) and triethanolamine (a product of the Union Carbide Corporation) (1.4 weight percent). The resulting melt is admixed with Stepanol WAT produced by the Stepan Chemical Company (35.0 weight percent). The resulting mixture is heated to 60° C. and mixed until a clear solution is obtained (at 60° C.). This material is "Composition A".

GAFQUAT® 755N polymer (manufactured by the GAF Corporation of 140 West 51st Street, New York, N.Y.) (5.0 weight percent) is admixed with 0.1 weight percent sodium sulfite and 1.4 weight percent polyethylene glycol 6000 distearate produced by the Armak Corporation. This material is "Composition B".

The resulting "Composition A" and "Composition B" are than mixed in a 50:50 weight ratio of A:B and cooled to 45° C. and 0.3 weight percent of perfuming substance as set forth in Table I of Example V is added to the mixture.. The resulting mixture is cooled to 40° C. and blending is carried out for an additional one hour in each case. At the end of this blending period, the resulting material has a pleasant fragrance as indicated in Table I of Example V.

EXAMPLE XIII

Scented polyethylene pellets having a pronounced scent as set forth in Table I of Example V are prepared as follows:

75 pounds of polyethylene of a melting point of about 220° F. are heated to about 230° F. in a container of the kind illustrated in FIGS. 6 and 7. 25 pounds of each of the perfume materials of Table I of Example V, supra, are then added quickly to the liquified polyethylene. The lid 228 is put in place and the agitating means 273 are actuated. The temperature is maintained at about 225° F. and the mixing is then continued for about 5–15 minutes. The valve "V" is then opened to allow flow of the molten polyethylene enriched with each of the aroma substance-containing materials to exit through the orifices 234. The liquid falling through the orifices 234 solidify almost instantaneously upon impact with the moving, cooled conveyor belt 238. Solid polyethylene beads or pellets 244 having pronounced aromas as set forth in Table I of Example V, supra, are then formed. Analysis demonstrates that the pellets contain about 25% of each of the perfume substances of Table I of Example V so that almost no losses of the scenting substance occurs. These pellets may be called master pellets.

50 pounds of the scent-containing master pellets are then added to the 1,000 pounds of unscented polyethylene powder and the mass is heated to the liquid state. The liquid is molded into thin sheets or films. The sheets or films have a pronounced aroma as set forth in Table I of Example V, supra. The sheets are also fabricated into garbage bags which have aromas as set forth in Table I of Example V, supra.

What is claimed is:

1. A 3,5-dimethyl-pentenyl-dihydro-2(3H)-furanone isomer mixture defined according to the structure:

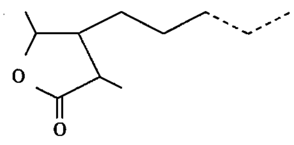

wherein in the mixture in each of the compounds one of the dashed lines is a carbon-carbon double bond and the other of the dashed lines is a carbon-carbon single bond.

2. A process for augmenting or enhancing the aroma of a consumable material selected from the group consisting of perfume compositions, perfumed articles and colognes comprising the step of intimately admixing with a perfume base, a perfumed article base or a cologne base an aroma augmenting, enhancing or imparting quantity of at least one compound defined according to claim 1.

3. A perfume composition comprising a perfume base and intimately admixed therewith an aroma augmenting, enhancing or imparting quantity of a composition defined according to claim 1.

4. A perfumed article comprising a perfumed article base and intimately admixed therewith an aroma augmenting, enhancing or imparting quantity of a composition of matter defined according to claim 1.

5. A cologne consisting essentially of water, ethanol and an aroma imparting quantity of a composition of matter defined according to claim 1.

6. A perfumed polymer comprising a microporous polymer and intimately admixed therewith and contained in the interstices thereof an aroma imparting quantity of a composition of matter defined according to claim 1.

* * * * *